(12) United States Patent
Geiselhart

(10) Patent No.: US 8,997,751 B2
(45) Date of Patent: Apr. 7, 2015

(54) SURGICAL INSTRUMENT

(75) Inventor: Franz Geiselhart, Reutlingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 983 days.

(21) Appl. No.: 13/005,407

(22) Filed: Jan. 12, 2011

(65) Prior Publication Data
US 2011/0112367 A1 May 12, 2011

Related U.S. Application Data

(60) Division of application No. 11/338,396, filed on Jan. 24, 2006, now Pat. No. 7,892,223, which is a continuation of application No. PCT/EP2004/008164, filed on Jul. 21, 2004.

(30) Foreign Application Priority Data

Jul. 29, 2003 (DE) .................... 103 34 562

(51) Int. Cl.
A61B 19/00 (2006.01)
A61B 1/12 (2006.01)
A61B 1/00 (2006.01)
A61B 1/015 (2006.01)
A61B 18/04 (2006.01)

(52) U.S. Cl.
CPC ............. *A61B 1/00068* (2013.01); *A61B 1/015* (2013.01); *A61B 1/12* (2013.01); *A61B 18/042* (2013.01); *A61B 2218/002* (2013.01)

(58) Field of Classification Search
USPC ............ 606/1, 2, 20–31, 41, 45, 49; 607/101, 607/104–107; 600/153–159; 128/898
See application file for complete search history.

(56) References Cited

U.S. PATENT DOCUMENTS

| | | | |
|---|---|---|---|
| 4,402,310 A | 9/1983 | Kimura | |
| 4,509,507 A * | 4/1985 | Yabe | ............................ 600/158 |
| 5,720,745 A | 2/1998 | Farin et al. | |
| 5,785,521 A * | 7/1998 | Rizoiu et al. | ..................... 433/29 |
| 5,951,779 A | 9/1999 | Koyanagi et al. | |
| 6,391,000 B1 | 5/2002 | Belikan et al. | |
| 6,428,507 B1 | 8/2002 | Farin et al. | |
| 6,475,217 B1 | 11/2002 | Platt | |
| 7,061,597 B2 | 6/2006 | Oberleitner et al. | |
| 2001/0039370 A1 | 11/2001 | Takahashi et al. | |
| 2005/0079094 A1 | 4/2005 | Mariotti et al. | |

FOREIGN PATENT DOCUMENTS

| | | | |
|---|---|---|---|
| DE | 3415837 C2 | 10/1986 | |
| DE | 4139029 A1 | 6/1993 | |
| DE | 43 32 070 A1 * | 3/1995 | ............ A61M 39/00 |
| DE | 4332070 A1 | 3/1995 | |
| DE | 19545528 A1 | 6/1997 | |
| EP | 1281413 A2 | 2/2003 | |
| EP | 1293169 A1 | 3/2003 | |
| JP | 63203130 A | 8/1988 | |

(Continued)

*Primary Examiner* — Ahmed Farah
(74) *Attorney, Agent, or Firm* — Dickstein Shapiro LLP

(57) ABSTRACT

A surgical instrument has a gas-delivery device to supply a noble gas or other inert gas to a tissue-treatment region and a rinsing device for rinsing a target region, in particular a tissue-treatment region. In the instrument the rinsing pressure is generated by the inert gas supplied by the gas-delivery device.

2 Claims, 3 Drawing Sheets

(56) References Cited

FOREIGN PATENT DOCUMENTS

| JP | 2159244 A | 6/1990 |
| JP | 5199979 A | 8/1993 |
| JP | 5269079 A | 10/1993 |
| JP | 7265259 A | 10/1995 |
| JP | 2003-111774 A | 4/2003 |
| JP | 2003126026 A | 5/2003 |
| WO | WO-0108577 A1 | 2/2001 |

* cited by examiner

SURGICAL INSTRUMENT

CROSS-REFERENCE TO RELATED APPLICATIONS

This application is a divisional of U.S. application Ser. No. 11/338,396, filed Jan. 24, 2006 now U.S. Pat. No. 7,892,223, which is a continuation of International Application No. PCT/EP2004/008164, filed Jul. 21, 2004, which was published in the German language on Feb. 10, 2005, under International Publication No. WO 2005/011483A1, which claims priority from German Application No. 103 34 562.0, filed Jul. 29, 2003, the entirety of which applications are hereing incorporated by reference.

BACKGROUND OF THE INVENTION

The invention relates to a surgical instrument as well as to a method of operating a rinsing device of the surgical instrument.

From German published patent application DE 41 39 029 A1 (counterpart: U.S. Pat. No. 5,720,745) a high-frequency surgical device is known that coagulates tissue and is used together with an endoscope. In this procedure an inert gas is conducted to the operation site through a tube that contains an electrode, and a high-frequency (HF) coagulation current is supplied to the electrode and to the tissue, so that between the electrode and the region of tissue there is formed a plasma flux that coagulates the tissue. In order to clean the operation site, a rinsing liquid is applied before, during and after the coagulation treatment, by passage through a working channel of the endoscope. Rinsing of the endoscope optics can also be performed, in order to maintain a clear field of view.

International application publication No. WO 01/08577 discloses a surgical instrument with an electrode constructed as a polypectomy loop. Argon gas is conducted to the operation site as a protective gas, to prevent smoke production while a polyp is being removed by an HF current. A rinsing device to serve the above functions is likewise present.

Many other kinds of surgical apparatus are known, in particular to be used within body cavities (e.g., also laser apparatus), that conduct an inert gas to the treatment region for the purposes mentioned above, and that contain rinsing devices. The construction of all such apparatus is extremely elaborate.

From German Patent DE 34 15 837 C2 a liquid-supplying device for endoscopes is known that comprises an air pump by way of which pressure can be applied to a liquid container, in order to supply the endoscope with rinsing liquid or, alternatively, air. This device, too, has an elaborate construction.

From German published patent application DE 43 32 070 A1 a device for perfusing a body cavity is known in which a rinsing liquid contained in a disposable bag within a pressure container is conducted to the perfusion instrument by air pressure generated by a pressure source. This device is likewise elaborate.

From U.S. Pat. No. 5,785,521 a surgical instrument (in this case an instrument for laser surgery) known having a gas-delivery device to supply an inert gas to a tissue-treatment region and a rinsing device for rinsing a target region. A rinsing stream of rinsing liquid is put under a rinsing pressure by the inert gas supplied by the gas-delivery device. However, in the case of this device the rinsing process cannot be precisely controlled.

BRIEF SUMMARY OF THE INVENTION

It is an object of the present invention to provide a surgical instrument of the kind described at the outset that has a simplified construction, as well as to provide a method of operating the instrument.

According to the present invention there is provided a surgical instrument comprising a gas-delivery device to supply an inert gas to a tissue-treatment region, a rinsing device for rinsing a target region with a rinsing stream of a rinsing liquid that is put under a rinsing pressure by the inert gas supplied by the gas-delivery device, a first control that is adapted to be controlled in such a way that at least one of the pressure and the volume flow of the inert gas can be switched between at least one first value, for supplying the inert gas to the tissue-treatment region, and a second value for producing the rinsing pressure.

Hence, according to the present invention, the gas-delivery device that is present in such a surgical instrument is used to generate the rinsing pressure, so that separate pump devices for the rinsing liquid can be eliminated. This means not only that the construction of the apparatus can be considerably simplified, but also that the apparatus is simpler to operate and more fail-safe, because there is no need for separate pump devices. Furthermore, the gas-supply device comprises a control for regulating a pressure and/or a volume flow of the inert gas, so that owing to this control the "admission pressure" of the rinsing liquid can be simply controlled by switching the pressure and/or volume flow between a first value, for applying the inert gas to the tissue-treatment region, and a second value for generating the rinsing pressure. As a result the control can be used in two ways, first to regulate the pressure of the gas that is applied to the treatment region and second to place the rinsing liquid under a different pressure, as may be needed for rinsing.

Preferably a second control is provided to regulate a pressure and/or volume flow of the rinsing liquid. As a result, the rinsing process—starting with a maximal admission pressure—can be adjusted, so that the operator can produce exactly the desired effect.

Preferably, a filter device is provided for filtering the inert gas, so that it is germ-free. This increases the patient's safety.

In an especially preferred embodiment of the invention, a pressure container is provided, so that the rinsing liquid can be poured in and the pressurized inert gas can be introduced in such a way that the pressure of the inert gas is applied to the rinsing liquid. This exertion of pressure on the rinsing liquid can occur directly in the pressure container, if the pressure container is equipped with an ascending pipe (for the rinsing liquid). Preferably, however, an internal container to receive the rinsing liquid is provided, with an elastic wall that separates the rinsing liquid from the inert gas. Then the pressure container can remain on site (e.g., in a transportable stand for the surgical instrument) when the rinsing-liquid container is exchanged. Furthermore, contamination of the rinsing liquid by the inert gas or by the pressure container is thus precluded. In this case, it is especially preferred for the internal container to have the form of a commercially available infusion bag. Such infusion bags, filled with a sterile solution suitable to serve as rinsing liquid, are available in every hospital.

In a preferred embodiment of the invention, a mixer is provided to mix the inert gas with the rinsing liquid. This allows the amount of rinsing liquid to be reduced with no substantial deterioration of its cleaning action. This is made possible, for example, when the mixer comprises a foam-generating means, so that foam is squirted out of a nozzle in the rinsing device, and after it has emerged from the nozzle its bubbles burst so that a rinsing stream divided into fine droplets is produced.

Alternatively or additionally, the mixer can comprise a switch for switching between inert gas and rinsing liquid, which is constructed in such a way that inert gas and rinsing liquid are supplied to the surgical instrument in alternation.

This results in an additional reduction in the amount of rinsing liquid required. The switch in this case is preferably constructed in such a way that substantially equal volumes of rinsing liquid are accelerated by the pressure of the inert gas, and are "shot" (propelled) one after another onto the target area. Such a rinsing device is known per se, for example, from German patent document DE 195 45 528 (counterpart: U.S. Pat. No. 6,428,507).

Preferably, the surgical instrument is an HF surgical instrument, because in the case of such equipment, in particular for employment in body cavities, a source of compressed gas is present, namely a pressure bottle with argon gas. It is likewise preferred to construct the surgical instrument as an instrument for laser surgery, because in this case, again, an inert gas is used to great advantage.

The present invention, as a whole, thus also applies to a method for operating a rinsing device for a surgical instrument, wherein a pressurized gas is conveyed to a rinsing-liquid container in such a way that the rinsing liquid is placed under a rinsing pressure. Hence, compressed air, such as is customarily available in operating rooms, can also be used as the pressurized gas. This simplifies the pressure generation, in particular when (as described above) the rinsing liquid is present in an elastic container (in particular an infusion bag) and is set into a pressure container that is then placed under gas pressure.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

In the following description, the same reference numerals are used for identical parts or parts with identical actions.

DETAILED DESCRIPTION OF THE INVENTION

Figure 1:
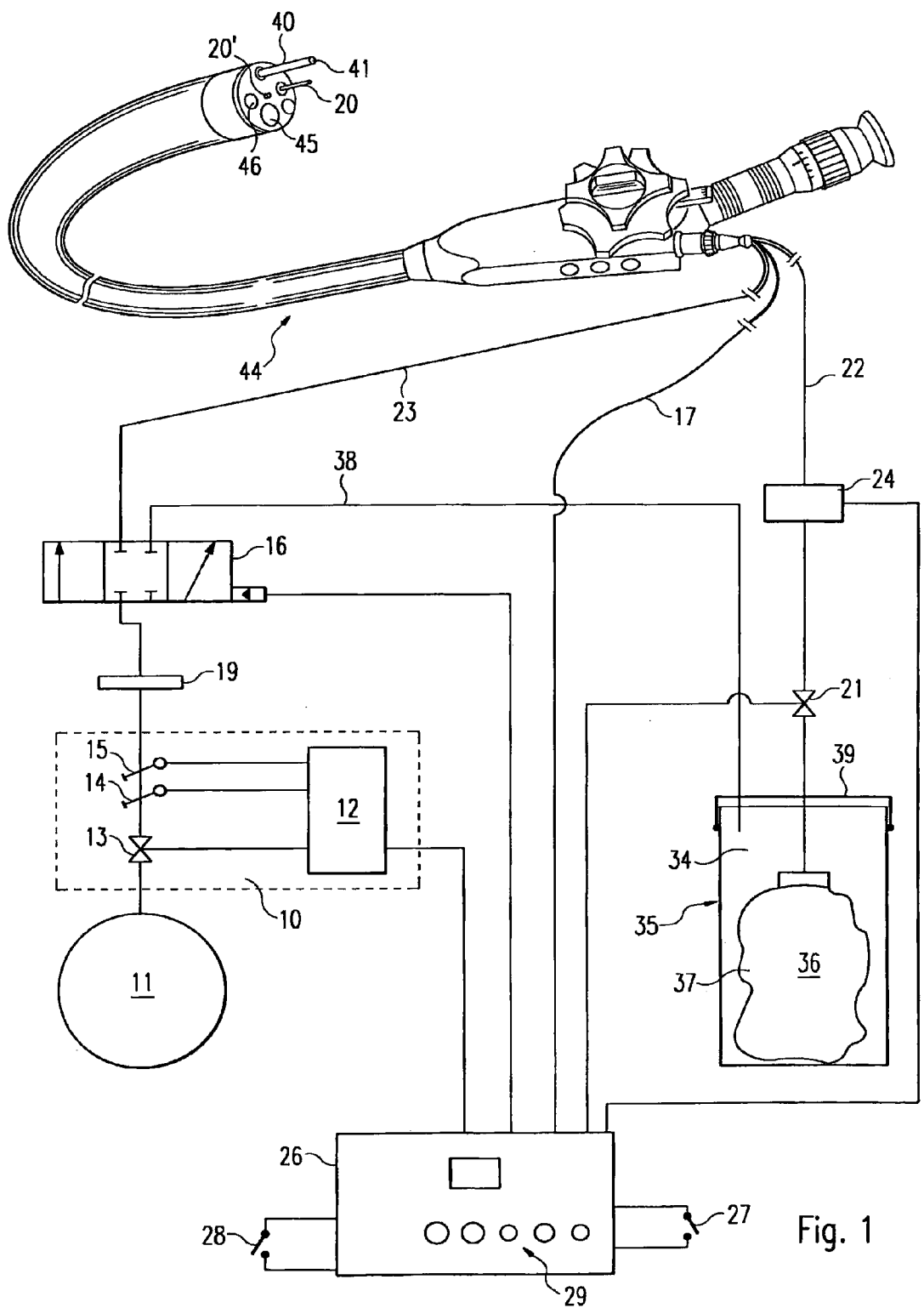
FIG. 1 is a block diagram illustrating a first embodiment of the invention.

FIG. 1 illustrates the arrangement in principle of a surgical appliance used with an endoscope 44. In this case the appliance is a so-called APS (argon-plasma surgery) probe, such as is known, for example, from German published patent application DE 41 39 029 A1 (U.S. Pat. No. 5,720,745).

As indicated in FIG. 1, the endoscope 44 comprises working channels 46 such that the actual surgical appliance 40, namely an APS probe with its open end serving as functional section 41, projects out of one working channel, while a rinsing device 20 projects from another working channel. A rinsing device 20' is also provided for an optical device 45 of the endoscope 44.

In order to deliver the inert gas, in particular argon or helium, from a gas bottle 11 by way of a gas-delivery device 10 and a gas conduit 23 to the APS probe 40, a proportional valve 13 is provided within the gas-delivery device 10 and is regulated by a first control 12 in conformity with signals from a pressure sensor 14 and a volume-flow sensor 15. The gas stream passing through a filter 19 and a three-way valve 16 (when in its position shown on the left) is regulated by the first control 12 with respect to its pressure and its volume per unit time, in such a way that a uniform flow of argon, appropriate for the purposes of the momentary application, flows out of the APS probe 40.

To adjust the values (pressure, volume flow, on/off) of the gas stream, as well as an HF coagulation current that is supplied by way of an HF current-conductor of the APS probe 40, a surgery device 26 is provided that comprises adjustment organs 29 and a (foot-)switch 28. When the foot-switch 28 is actuated, initially the valve 16 responds so that the gas stream can flow through the conduit 23 into the APS probe 40 before the coagulation current is turned on. This is known per se.

In addition a pressure conduit 38 is provided, which (when the valve 16 is in the right-hand position) guides the pressurized inert gas into a pressure container 35 that is closed in a gas-tight manner by a cover 39. Within the pressure container 35 is an internal container 36, in particular an infusion bag filled with Ringer solution, which includes an elastic wall 37. A rinsing conduit 22 is attached to the inner container 36 in such a way that, when pressure is introduced into the pressure container 35, the elastic wall 37 of the inner container 36 is pressed inwardly and, therefore, the liquid within the inner container is pressed out, into the rinsing conduit 22.

Inserted into the rinsing conduit 22 are a rinsing valve 21 (on/off) and a second control 24, both of which can be controlled by associated control leads from the surgery device 26. The rinsing valve 21 can be turned on and off by a rinsing switch 27 (actuated, e.g., with the foot), whereas the flow parameters, in particular the pressure and the volume flow (volume/time) of the rinsing solution, are adjustable by way of the adjustment organs 29 of the surgery device 26 and the second control 24.

The valve 16 is preferably actuated in such a way that the inert gas is conducted either to the surgical instrument 40 or to the pressure container 35. Alternatively, of course, it is possible to connect the conduit 38 at a point directly after the filter 19 or even to the gas bottle 11, so that either the pressure determined by the first control 12 or the gas-bottle pressure (where appropriate, by way of a pressure-reducing valve) is conducted to an internal space within the pressure container 35, and the control of the rinsing-liquid stream is accomplished exclusively by the rinsing valve 21 and/or the second control 24.

Figure 2:
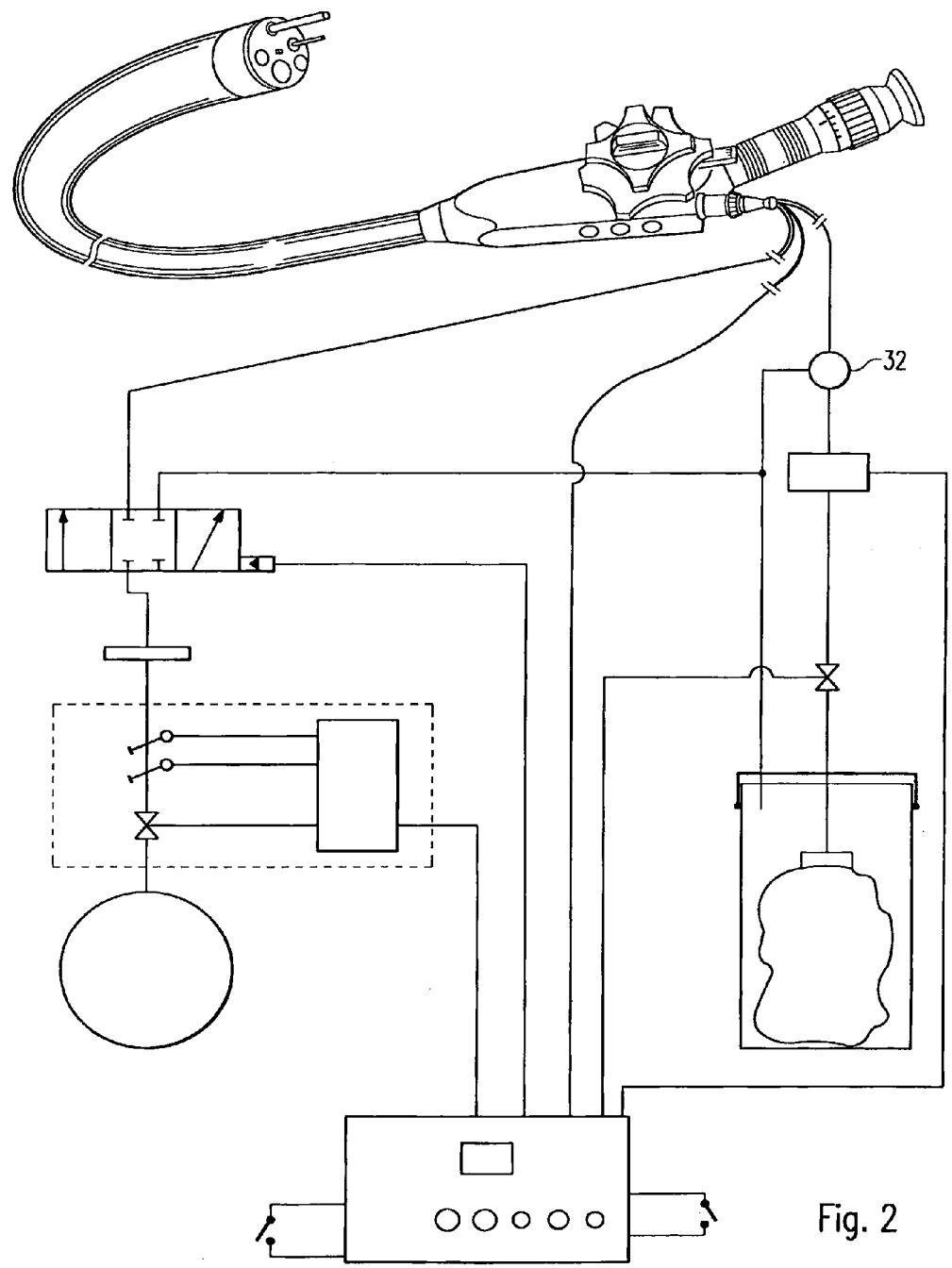
FIG. 2 is diagram, similar to FIG. 1, illustrating another embodiment of the invention.

In the embodiment shown in FIG. 2 there is provided, in addition to the parts shown in FIG. 1, a foam-generator 32 that mixes the rinsing liquid with inert gas, so that the amount of rinsing liquid can be reduced, although its rinsing properties are not appreciably changed.

Figure 3:
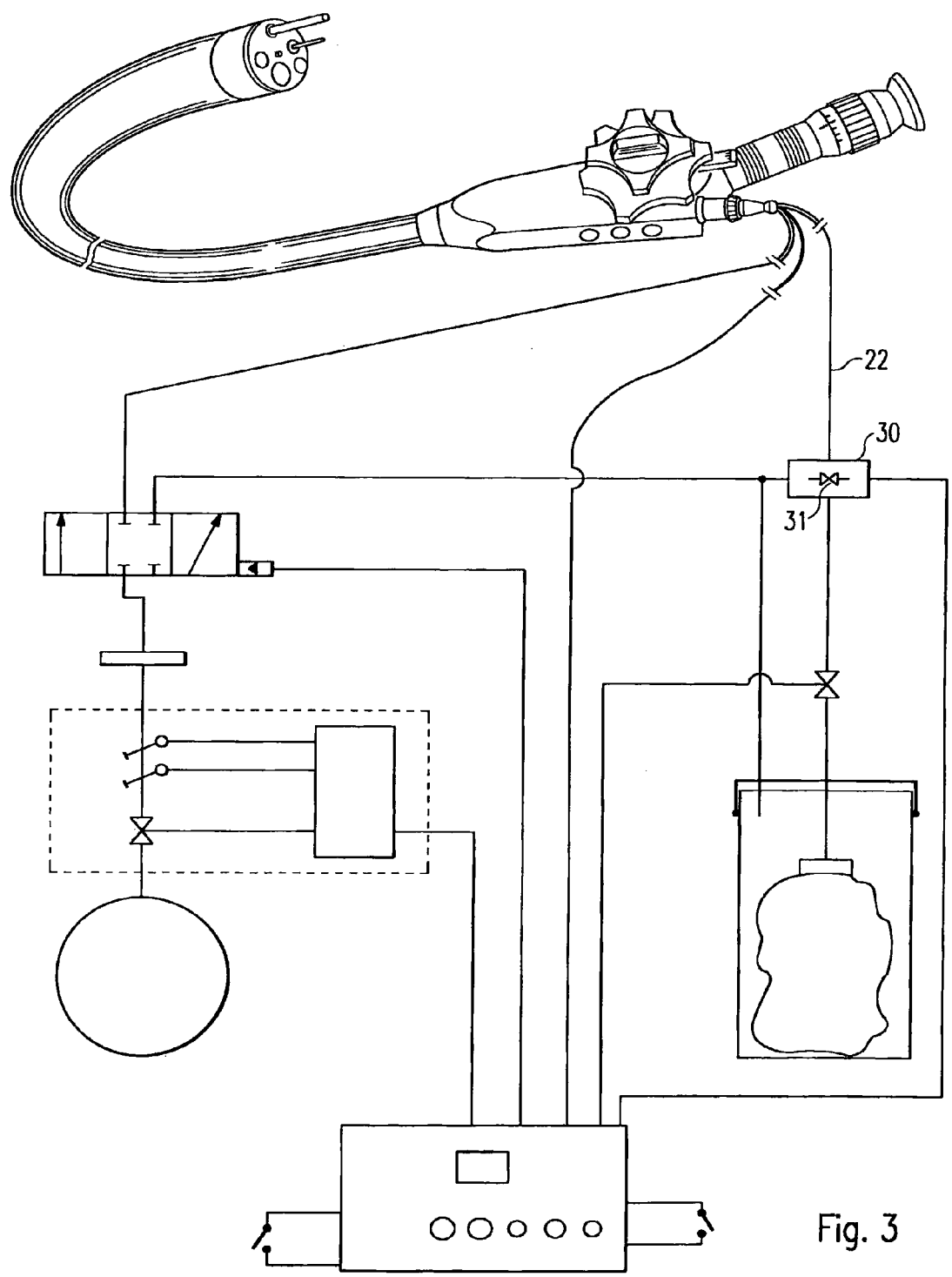
FIG. 3 is a diagram, similar to FIG. 1, illustrating a third embodiment of the invention.

In the embodiment of the invention shown in FIG. 3, in place of the foam-generator 32, a mixer 30 is provided, which comprises a switch 31 to enable switching between inert gas and rinsing liquid in such a way that small "slugs" of rinsing liquid are guided through the rinsing conduit 22 with pressurized gas volumes behind them, and thus are accelerated until they are ejected from the rinsing device 20, i.e., from its end. This can, of course, also be combined with the embodiment according to FIG. 2, in such a way that "slugs" of foam are accelerated and ejected by the cushions of gas behind them. The regulation of the rinsing pressure by the second control 24, as shown in FIG. 1, can likewise take place here.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method of operating a rinsing device for a surgical instrument, comprising the steps of:
   filling an internal rinsing-liquid container having an elastic wall with a rinsing liquid;
   delivering a pressurized inert gas from a gas-delivery device via a conduit to an external rinsing-liquid container inside of which is the internal rinsing-liquid container;
   placing the rinsing liquid under a rinsing pressure by the pressurized inert gas by the action of the gas directly upon the elastic wall of the internal rinsing-liquid container;
   regulating at least one of a pressure and a volume flow of the inert gas; and
   switching at least one of the pressure and the volume flow of the inert gas between a first value for supplying the inert gas to a tissue-treatment region and a second value for supplying the inert gas to produce the rinsing pressure.

2. The method according to claim 1, wherein said regulating is effected in accordance with signals from a pressure sensor and a volume flow sensor.

* * * * *